(12) United States Patent
Van Liere (10) Patent No.: US 11,083,869 B2
(45) Date of Patent: Aug. 10, 2021

(54) BRAIDED CRESCENT RIBBON CATHETER REINFORCEMENT

(71) Applicant: Bard Peripheral Vascular, Inc., Tempe, AZ (US)

(72) Inventor: Chad Van Liere, Phoenix, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 1056 days.

(21) Appl. No.: 14/659,464

(22) Filed: Mar. 16, 2015

(65) Prior Publication Data

US 2016/0271362 A1  Sep. 22, 2016

(51) Int. Cl.
*A61M 25/00* (2006.01)

(52) U.S. Cl.
CPC ...... *A61M 25/0053* (2013.01); *A61M 25/005* (2013.01)

(58) Field of Classification Search
CPC ............ A61M 25/0053; A61M 25/005; A61M 25/0054
See application file for complete search history.

(56) References Cited

U.S. PATENT DOCUMENTS

| | | | | |
|---|---|---|---|---|
| 5,676,659 | A | * | 10/1997 | McGurk .......... A61M 25/0012 138/124 |
| 5,685,841 | A | * | 11/1997 | Mackool ............. A61F 9/00745 604/22 |
| 6,217,565 | B1 | | 4/2001 | Cohen |
| 7,850,623 | B2 | | 12/2010 | Griffin et al. |
| 2003/0191451 | A1 | * | 10/2003 | Gilmartin .......... A61M 25/005 604/527 |
| 2005/0033311 | A1 | | 2/2005 | Guldfeldt et al. |
| 2007/0100285 | A1 | * | 5/2007 | Griffin ............. A61M 25/0013 604/164.11 |
| 2010/0168716 | A1 | | 7/2010 | Von Weymarn-Scharli |
| 2015/0141760 | A1 | * | 5/2015 | Chou ................ A61B 17/0057 600/204 |

FOREIGN PATENT DOCUMENTS

| | | |
|---|---|---|
| EP | 2389973 A1 | 11/2011 |
| WO | WO2014203336 A1 | 12/2014 |

OTHER PUBLICATIONS

Noone, D.: Experimental and Numerical Investigation of Wire Waveguides for Therapeutic Ultrasound Angioplasty. M.Eng. Dublin City University. 2008.

* cited by examiner

*Primary Examiner* — Emily L Schmidt
(74) *Attorney, Agent, or Firm* — Dickinson Wright PLLC (57) ABSTRACT

A catheter comprising a base material, an optional body material, and a braid structure having crescent-shaped ribbons braided into the structure. Various biocompatible polymers can function as base or body materials. When a ribbon is metallic, various biocompatible materials can function in the ribbon. The crescent of a crescent ribbon can face luminally or abluminally.

26 Claims, 9 Drawing Sheets

BRAIDED CRESCENT RIBBON CATHETER REINFORCEMENT

BACKGROUND

Catheters with polymeric walls and wire reinforcement are known. In some cases, these wire reinforcements take the shape of ribbons in that they have a substantially rectangular cross-section. These catheters have increased stiffness compared to similar catheters lacking the braid structure.

Sometimes these ribbons are braided before a manufacturer incorporates them into a catheter. The increased longitudinal and torsional stiffness brought about by reinforcing structure allows for a smaller diameter catheter while preserving the catheter's stiffness.

Since there is an ever-present need for smaller diameter catheters, what is needed is a braid structure with a higher degree of stiffness.

SUMMARY

Various embodiments of a catheter having a base material, in some cases a polymeric base material, and a braid structure having a plurality of crescent-shaped ribbons disposed about the catheter's lumen or axis are disclosed. Some embodiments employ a braided structure such that the concave side of the ribbons faces inwardly; some embodiments employ a braided structure such that the concave side faces outwardly; some embodiments employ a braided structure with a combination of inwardly and outwardly facing ribbons. Some embodiments employ a braided structure such that the concave side of the ribbons faces luminally; some embodiments employ a braided structure such that the concave side faces abluminally; some embodiments employ a braided structure with a combination of luminally and abluminally facing ribbons.

In various embodiments, the ribbons comprise a polymer or polymer mixture. Other embodiments employ at least one ribbon that is a metal or metal combination (such as alloys). Some embodiments select any one or any combination of biocompatible metals. In some cases, at least one ribbon uses a cold-worked metal, a stressed metal, or an annealed metal.

In these or other embodiments, the base material is any one or any compatible combination of polyurethanes, silicones, polyethers, thermoset polymeric material, polyesters, polyamides, fluoropolymers, polyolefins, PVC, polyimides, or PEEK.

As the ribbons can comprise a variety of metals, in various embodiments, the base material is any one or any combination of biocompatible polymers and copolymers. Unless an incompatibility exists between a polymer or combination and a metal or combination, embodiments combining any combination of metals and polymers are within the invention's scope.

In some embodiments, the base material has a film-like construction. Depending on the particular embodiment, the film contacts the braid structure on an inside of the braid structure, on an outside of the braid structure, or on the inside and the outside of the braid structure.

In some film embodiments, the base material is any one or any combination of conventional biocompatible polymers and copolymers and the ribbon consists essentially of a metal or metal combination.

In some embodiments, the base material is any one or any combination of polyurethanes, silicones, polyethers, thermoset polymeric material, polyesters, polyamides, fluoropolymers, polyolefins, PVC, polyimides, or PEEK, and the ribbon consists essentially of a metal or metal combination.

COMPONENT KEY

Ribbon or Reinforcing member, 100
Long face of ribbon, 120
Long edge of ribbon, 130
Short edge of ribbon, 140
Crescent-shaped ribbon reinforcing member, Crescent ribbon reinforcing member, crescent ribbons, or crescent-shaped reinforcing member, 210
Crescent ribbons 210 with concave face 250 positioned luminally, 210L
Crescent ribbons 210 with concave face 250 positioned abluminally, 210A
Convex face of crescent ribbon, 220
Crescent end of crescent ribbon, 240
Concave face of crescent ribbon, 250
Prior-art reinforced catheter, 300
Abluminal surface of catheter, 310
Luminal surface of catheter, 320
Wall of catheter, 330
Catheter with luminally facing crescent-shaped reinforcing members 210L embedded in body material, 400
Catheter with braided arrangement of crescent ribbons 210, 500
Catheter with abluminally facing crescent ribbons 210A, 600
Device of braided crescent ribbons 210A, 700

DETAILED DESCRIPTION

The following describes non-limiting examples that further illustrate the invention. No section titles, including those appearing above, are limitations on the invention, but rather they provide structure to the illustrative descriptions that the specification provides. The features, aspects, and advantages of the invention will become more apparent from the following detailed description, appended claims, and accompanying drawings.

Unless defined otherwise, all technical and scientific terms used in this document have the same meanings that one skilled in the art to which the disclosed invention pertains would ascribe to them. The singular forms "a", "an", and "the" include plural referents unless the context clearly indicates otherwise. Thus, for example, reference to "a fluid" refers to one or more fluids, such as two or more fluids, three or more fluids, etc. Any mention of an element includes that element's equivalents as known to those skilled in the art.

The figures are not necessarily drawn to scale, and in some instances the drawings exaggerate or simplify the invention for illustrative purposes. One of ordinary skill in the art will appreciate the many possible applications and variations of the present invention based on the following examples of possible embodiments of the present invention.
Components 100, 120, 130, 140, 210, 220, 240, and 250

Figure 1:
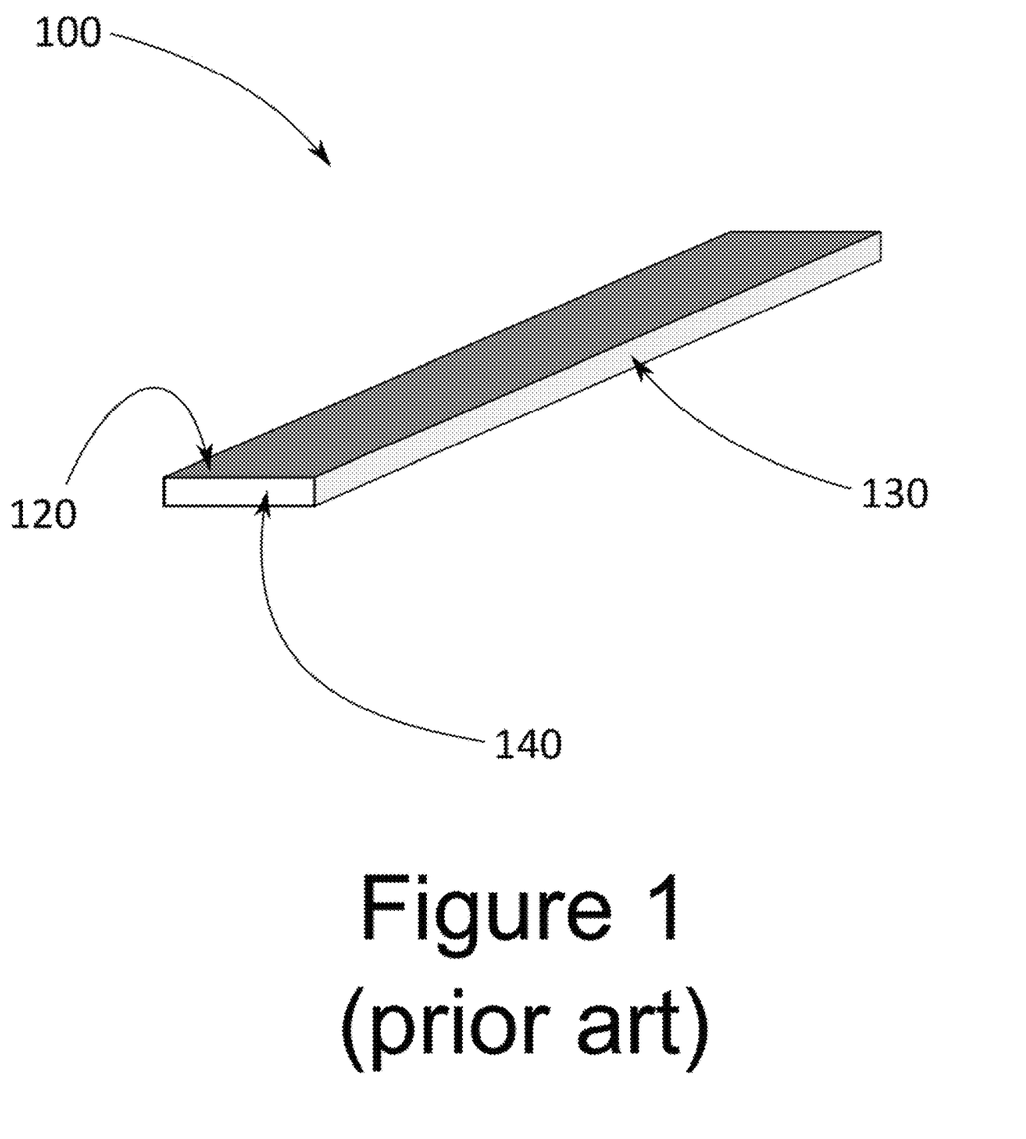
FIG. 1 is a perspective view of a prior art ribbon

Prior-art FIG. 1 depicts ribbon 100 with long face 120, long edge 130, and short edge 140.

Figure 2:
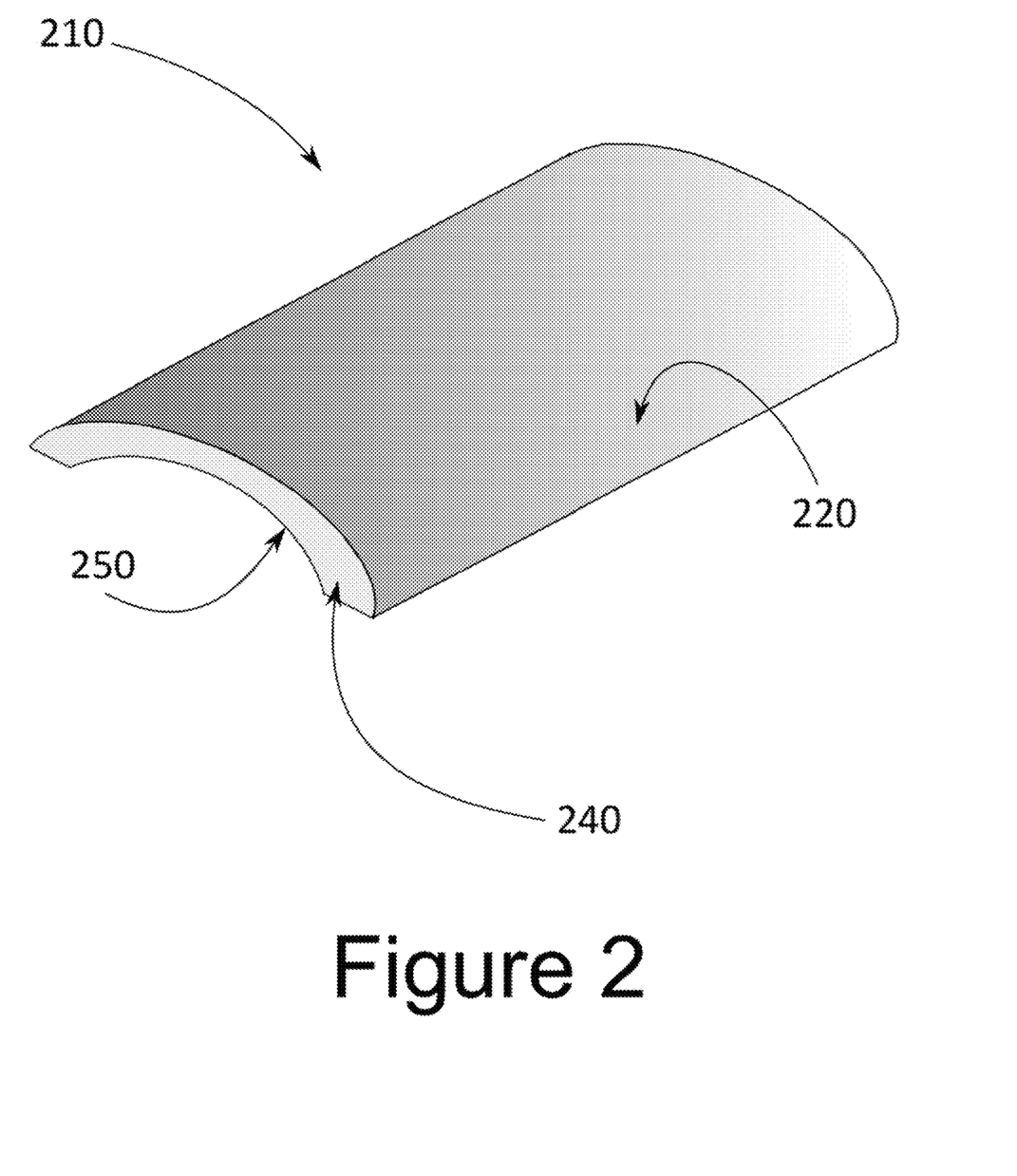
FIG. 2 is a perspective view of a ribbon of the invention.

FIG. 2 depicts crescent ribbon 210, which replaces reinforcing member 100 in invention embodiments. Crescent ribbon 210 comprises convex face 220, crescent end 240, and concave face 250. By definition crescent ribbon 210 exhibits curvature in lines perpendicular to a longitudinal axis of the ribbon, while lines parallel to the longitudinal axis of the ribbon are substantially straight.
Components 300, 310, 320, and 330

Figure 3:
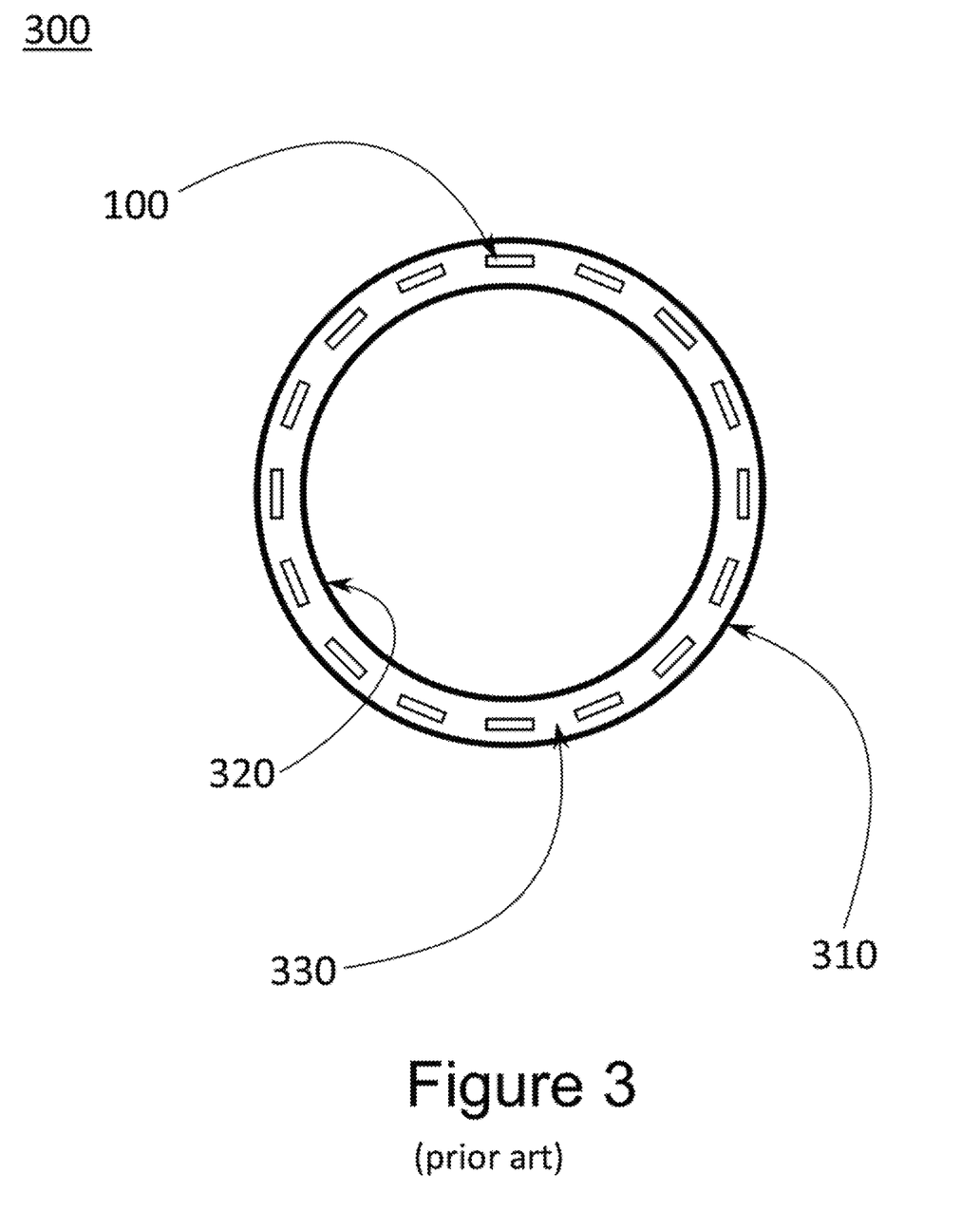
FIG. 3 is a cross sectional view of a prior art catheter.

FIG. 3 depicts a longitudinal cross-section of a prior art reinforced catheter 300. Catheter 300 comprises abluminal surface 310, luminal surface 320, wall 330, and reinforcing member 100. Typically, this arrangement of components allows catheter 300 to exhibit sufficient strength or stiffness while using smaller diameters or less material or both. Somewhat concealed in a cross-sectional view, a plurality of reinforcing member 100 are known to successfully reinforce a catheter when those reinforcing members 100 are arranged longitudinally or helically. The plurality of other reinforcing members 100 can be arranged in braided or woven structures.

Figure 4:
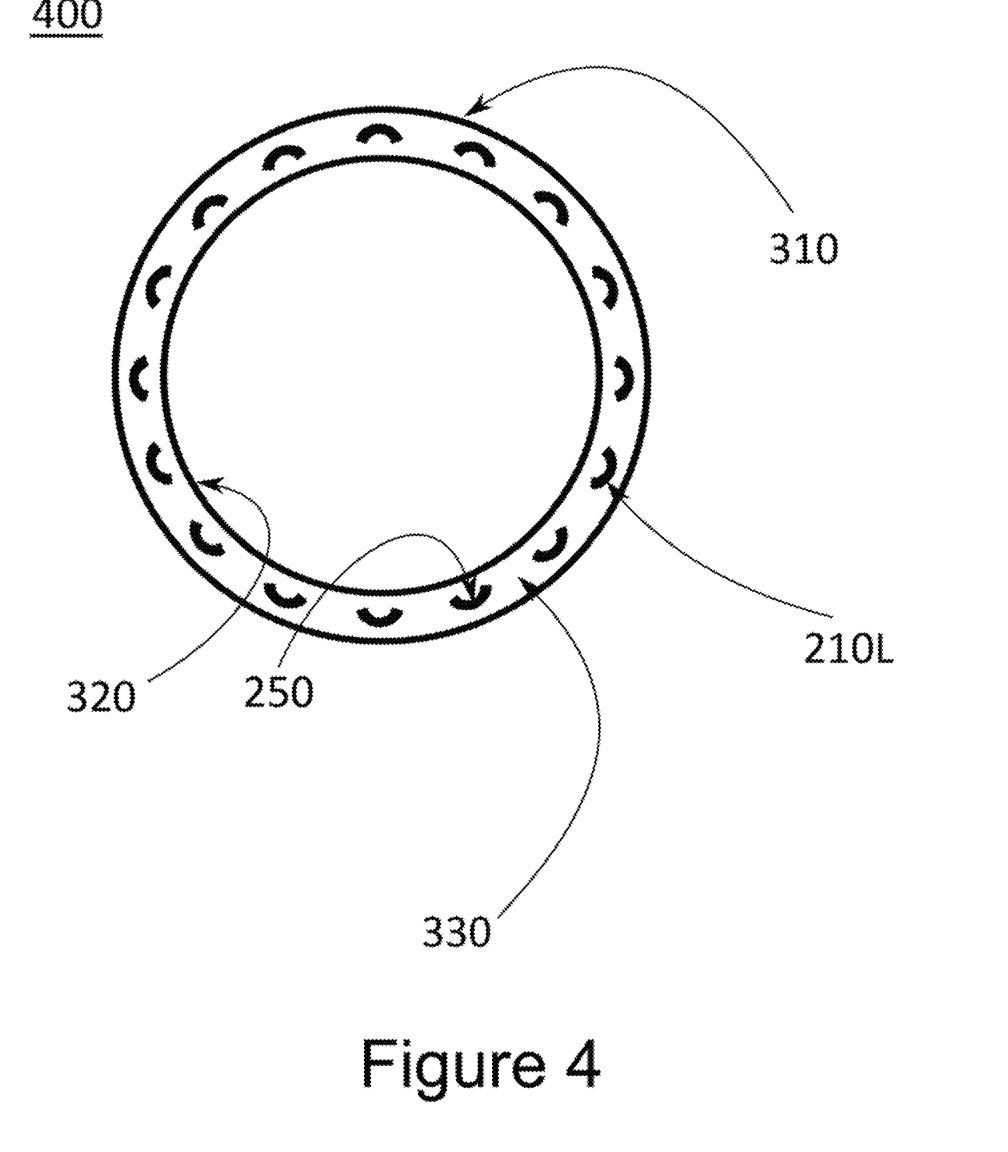
FIG. 4 is a cross sectional view of an invention catheter having luminally facing crescent-shaped ribbons.

Wall 330 comprises any material known to be useful for constructing the body of a reinforced catheter. For purposes of this disclosure, useful materials are called "body material" and are discussed more fully below. For purposes of this disclosure, "base material" is the material that contacts the crescent ribbons. It may be the same as or different from "body material".
Components 400 and 210L FIG. 4 depicts an invention embodiment comprising a catheter 400 with several luminally facing crescent-shaped ribbon or crescent ribbons 210L functioning to reinforce catheter 400. For purposes of this disclosure, luminal means facing the inside space of a body lumen. FIG. 4 depicts the embodiment in cross-section. Various embodiments exist in which the number of crescent ribbons 210L ranges from 1-100, 5-90, or 10-80. In these or other embodiments crescent ribbon 210L sits so that concave face 250 faces luminally—concave face 250 faces luminal surface 320. And wall 330 runs the length of catheter 400 while containing crescent ribbon 210L. In these or other embodiments, crescent ribbon 210L can be as long as or longer or shorter than catheter 400. Specifically, some embodiments employ crescent ribbons 210L that are 100%, greater than 90%, greater than 80%, greater than 70%, or greater than 60% of the length of catheter 400.

In some embodiments, wall 330 comprises body material. In some embodiments, crescent ribbons 210L are disposed in wall 330 such that the distance to luminal surface 320 is smaller than the distance to abluminal surface 310. In other embodiments, the distance from crescent ribbons 210L to luminal side 310 is larger than the distance to abluminal surface 310. Ultimately, catheter 400 comprises wall 330 that has crescent ribbons 210L embedded in it. Crescent ribbons 210L strengthen catheter 400 allowing it to be made smaller without sacrificing performance such as strength and stiffness.

Catheter 400 can take various formats. In some formats, the reinforcements extend the whole length of catheter 400. Other formats exhibit reinforcing member 210L along a portion of catheter 400. This portion can be 1, 2, 3, 4, 5, 10, 15, 20, 30, 40, 50, 60, 70, 80, 90, 95, 98, or 99% of the length of catheter 400. When less than all of the length of catheter 400 is associated with reinforcing member 210L, the region associated with reinforcing member 100 can be located anywhere along the length of catheter 400 including adjacent either end of catheter 400, centered between ends or in regions within 5, 10, 20, or 25% of either end of catheter 400.

Sometimes reinforcing member 210L is braided with other reinforcing members 210L before becoming part of catheter 400.

Depending on the embodiment, the reinforcing members are completely embedded in base material, partially embedded in base material, resting on the outside of a catheter of base material, resting on the inside of a catheter of base material, covered on the inside with a film of base material, covered on the outside with a film of base material, or sandwiched between inside and outside films of base material.

In other embodiments, while much of catheter 400 doesn't change, crescent ribbons 210 are flipped along their longitudinal axes such that concave face 250 points outward toward abluminal surface 310—crescent ribbon 210A. For purposes of this disclosure, abluminal means facing away from the inside space of a body lumen.
Component 500

Some embodiments arrange crescent ribbons 210 into braided structures. Some embodiments arrange crescent ribbons 210L into a braided structure 505 with concave face 250 pointing luminally. An example of braided structure 505 appears in FIG. 5, which shows catheter 500 with the base layer removed to show the braided structure 505 in a perspective view. Some embodiments arrange crescent ribbons 210L and crescent ribbons 210A together into a braided structure 500.

Figure 5:
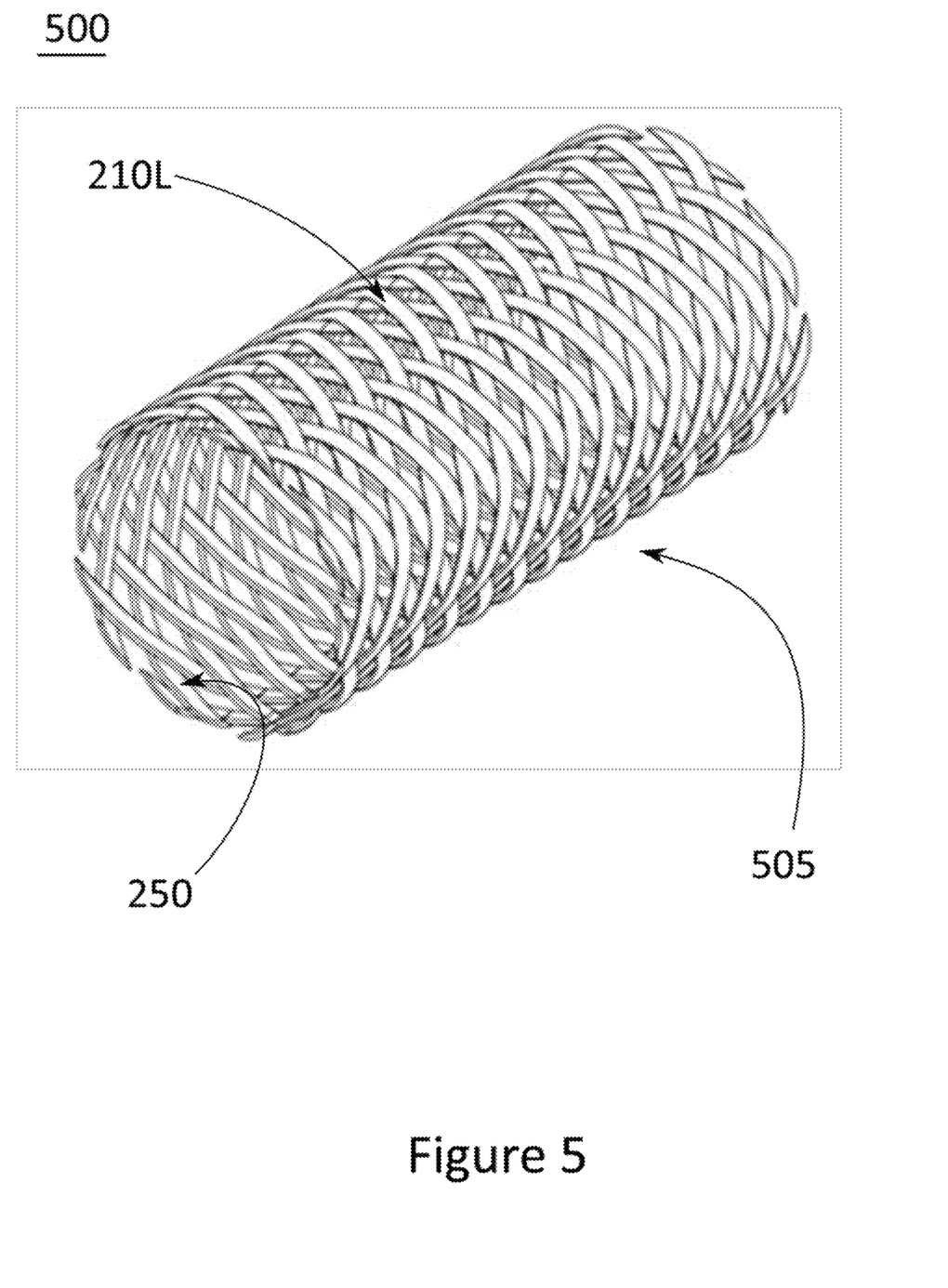
FIG. 5 is a cross sectional view of an invention catheter having luminally facing crescent-shaped ribbons.

Some related embodiments have approximately one crescent ribbon 210L for every 100 crescent ribbons 210A; one crescent ribbon 210L for every 50 crescent ribbons 210A; one crescent ribbon 210L for every 20 crescent ribbons 210A; one crescent ribbon 210L for every ten crescent ribbons 210A; one crescent ribbon 210L for every five crescent ribbons 210A; one crescent ribbon 210L for every two crescent ribbons 210A; one crescent ribbon 210L for every crescent ribbons 210L.

Figure 6:
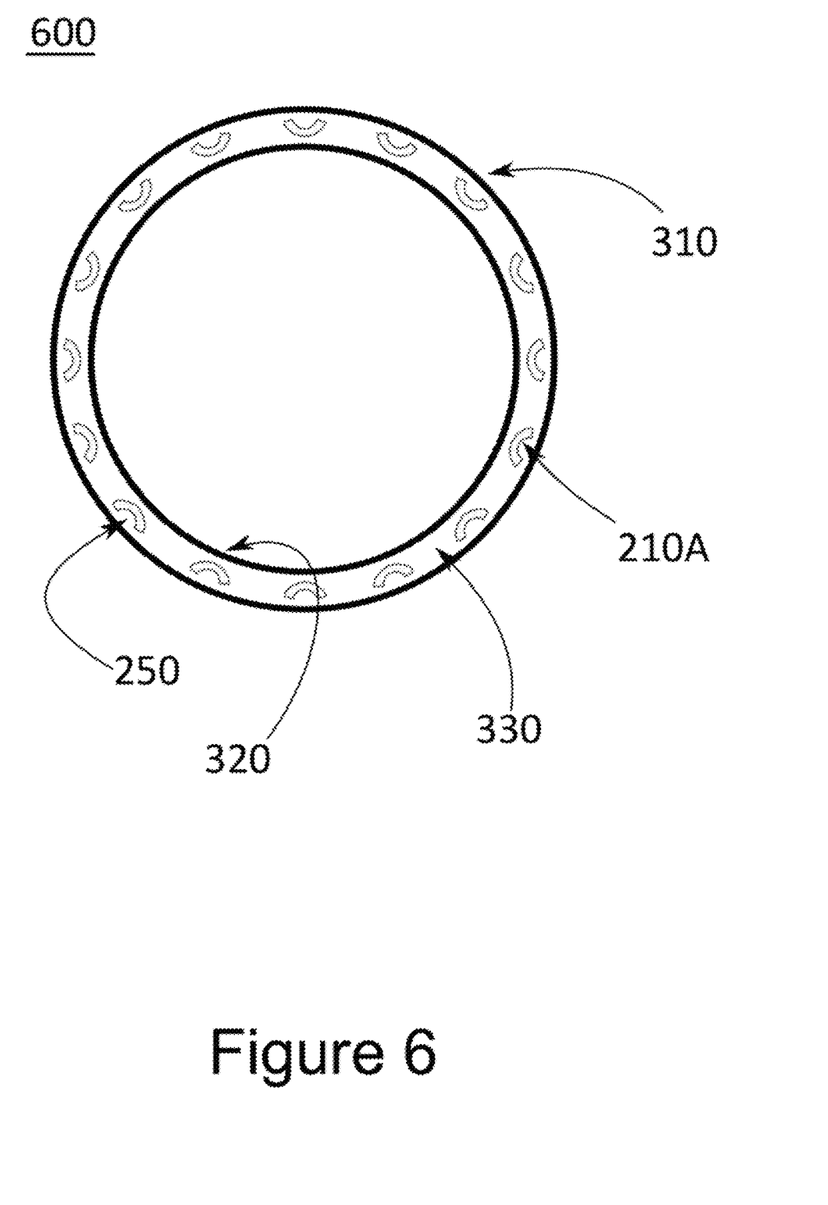
FIG. 6 is a perspective view of an invention braid structure with the concave side of the ribbon facing abluminally.

FIG. 6 depicts an invention embodiment with several crescent ribbons 210A functioning to reinforce catheter 600. Catheter 600 has a wall 330 having a luminal surface 320 and an abluminal surface 310. Crescent ribbons 210A are arranged in the structure with concave face 250 pointing outward. FIG. 6 depicts the embodiment in cross-section. Various embodiments exist in which the number of crescent ribbons 210A ranges from 1-100, 5-90, or 10-80. In these or other embodiments crescent ribbon 210A sits so that concave face 250 faces abluminally—concave face 250 faces abluminal surface 310, and wall 330 runs the length of catheter 600 while containing crescent ribbon 210A. In these or other embodiments, crescent ribbon 210A can be as long as or shorter than catheter 600. Specifically, some embodiments employ crescent ribbons 210A that are 100%, greater than 90%, greater than 80%, greater than 70%, or greater than 60% of the length of catheter 600.

Ultimately, catheter 600 comprises wall 330 that has crescent ribbons 210A embedded in it. Crescent ribbons 210A strengthen catheter 600 allowing it to be made smaller without sacrificing performance such as strength and stiffness.

Figure 7:
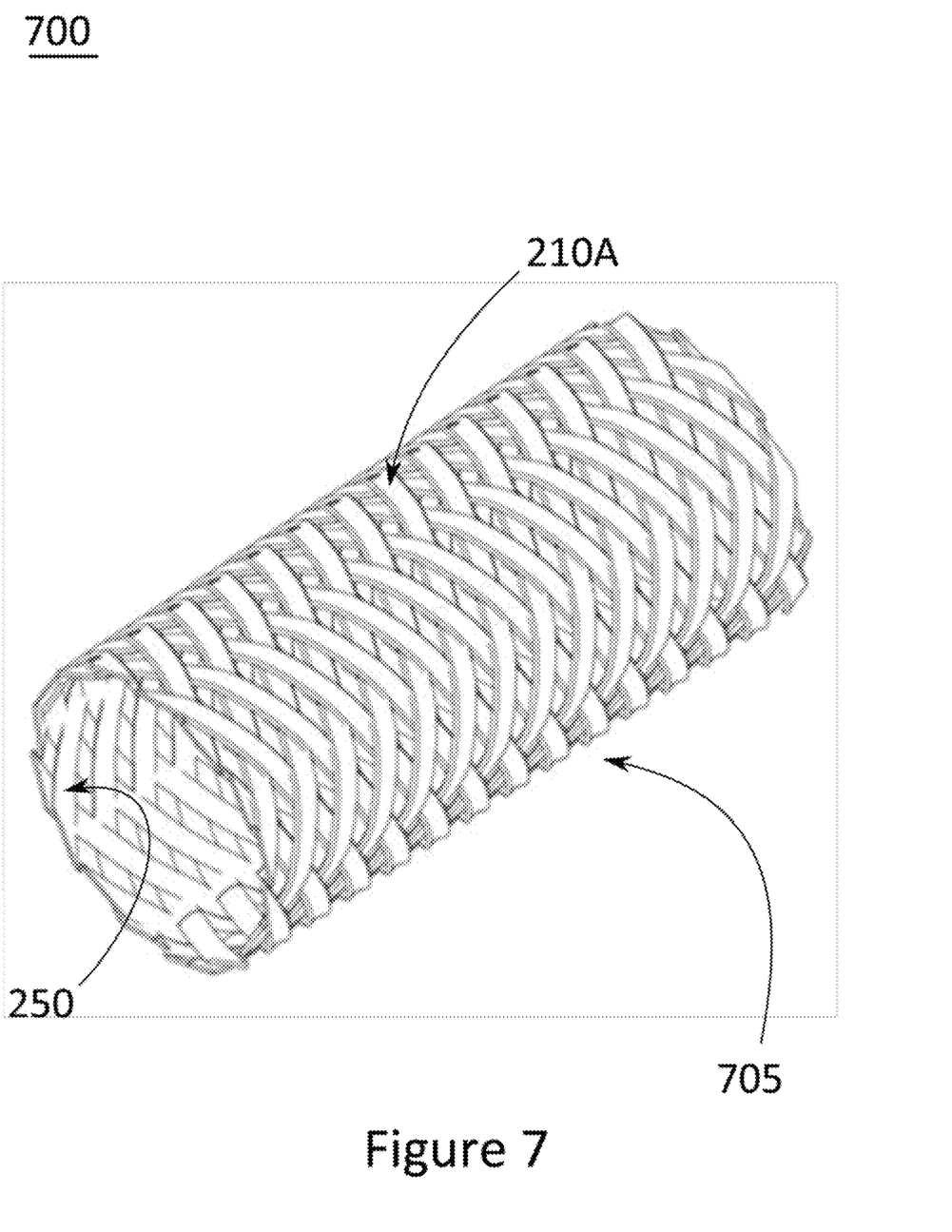
FIG. 7 is a perspective view of an invention braid structure with the concave side of the ribbon facing abluminally.

Reminiscent of braided structure 505, some embodiments have a braided structure such as braided structure 705 in which crescent ribbons 210A take a braided form and have concave face 250 pointing abluminally—this yields crescent ribbon or ribbons 210A. An example of braided structure 705 appears in FIG. 7, which shows catheter 700 with the base material removed to display braided structure 705 in a perspective view. Some related embodiments have approximately one crescent ribbon 210A for every 100 crescent ribbons 210L; one crescent ribbon 210A for every 50 crescent ribbons 210L; one crescent ribbon 210A for every 20 crescent ribbons 210L; one crescent ribbon 210A for every ten crescent ribbons 210L; one crescent ribbon 210A for every five crescent ribbons 210L; one crescent ribbon 210A for every two crescent ribbons 210L; one crescent ribbon 210A for every crescent ribbons 210A.

Various embodiments exist in which crescent ribbons 210 comprise a biocompatible material. In other embodiments in which wall 330 completely encapsulates crescent ribbon 210 or structures composed of crescent ribbon 210, biocompatibility isn't strictly necessary for materials composing crescent ribbons 210.

One way of forming the ribbons into crescent-shaped ribbons is by cold rolling the ribbon across appropriately shaped dies. Cold rolling improves the bend parameters independent of the improvements caused by the shape change.

In some cases "body material" is any one or any combination of biocompatible materials suitable for use as catheter wall components. In some cases "body material" is any one or any combination of conventional polymers and copolymers used in catheter wall construction. In some cases "body material" is any one or any combination of thermally weldable polymers. In some cases "body material" is any one or any combination of conventional biocompatible polymers. In some cases "body material" is any one or any combination of these polymers: polyurethanes, silicones, polyethers, thermoset polymeric material, polyesters, polyamides, fluoropolymers, polyolefins, PVC, polyimides, or PEEK. In these or other embodiments, body material comprises any one or any combination of these polymers: polyethylene, polyethylene terephthalate, polycaprolactam, ABS copolymers, polyester/polyether block copolymers, ionomer resins, liquid crystal polymers, rigid rod polymers, polyamide 12, polyether block amides (PEBA), polyetherester elastomers, high density polyethylenes (HDPE), polytetrafluoroethylenes (PTFE), poly(tetrafluoroethylene-co-perfluoroalkyl vinyl ether), perfluoropropyl vinyl ether, perfluoromethyl vinyl ether, fluorinated ethylene propylene (FEP), polyoxymethylene, polyoxymethylene blended with a polyether polyester, perfluoroelastomers, expanded polytetrafluoroethylene (ePTFE), or ultra-high-molecular-weight polyethylene.

In some cases "reinforcement material" is any one or any combination of biocompatible materials suitable for use catheter wall components. In some cases "reinforcement material" is any one or any combination of metals or alloys. Some embodiments employ "reinforcement material" that are any one or any combination of biocompatible metals or alloys. For example, some embodiments employ Series 300 stainless steel as the "reinforcement material". Finally, some embodiments consist essentially of metals or alloys. The reinforcement material can be cold worked during the formation of the crescent shape. In these types of embodiments, the material is specifically defined to be cold worked. This means that the metal has the internal stresses or strains typically found in cold worked metals. In some embodiments, the metal is used with or without post-form annealing. Metal that is annealed after forming is specifically defined as annealed metal. Metal that is not annealed is specifically defined as stressed metal.

Construction Methods

Methods of constructing invention composite catheters are well known to those of ordinary skill in the art. In some embodiments, the catheter is constructed by extruding the catheter base material over crescent ribbons 210. In these or other embodiments, the base material is combined with crescent ribbons 210 using dip casting, over-molding, solution casting, or multilumen extruding and bonding.

The base material includes an ePTFE substrate in some embodiments. As is known in the art, an ePTFE substrate may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc. Other methods for forming an ePTFE substrate in the present invention are possible and are within the scope of the invention.

EXAMPLES

Finite Element Analysis (FEA)

The FEA software is ANSYS version R15.0.

Figure 8:
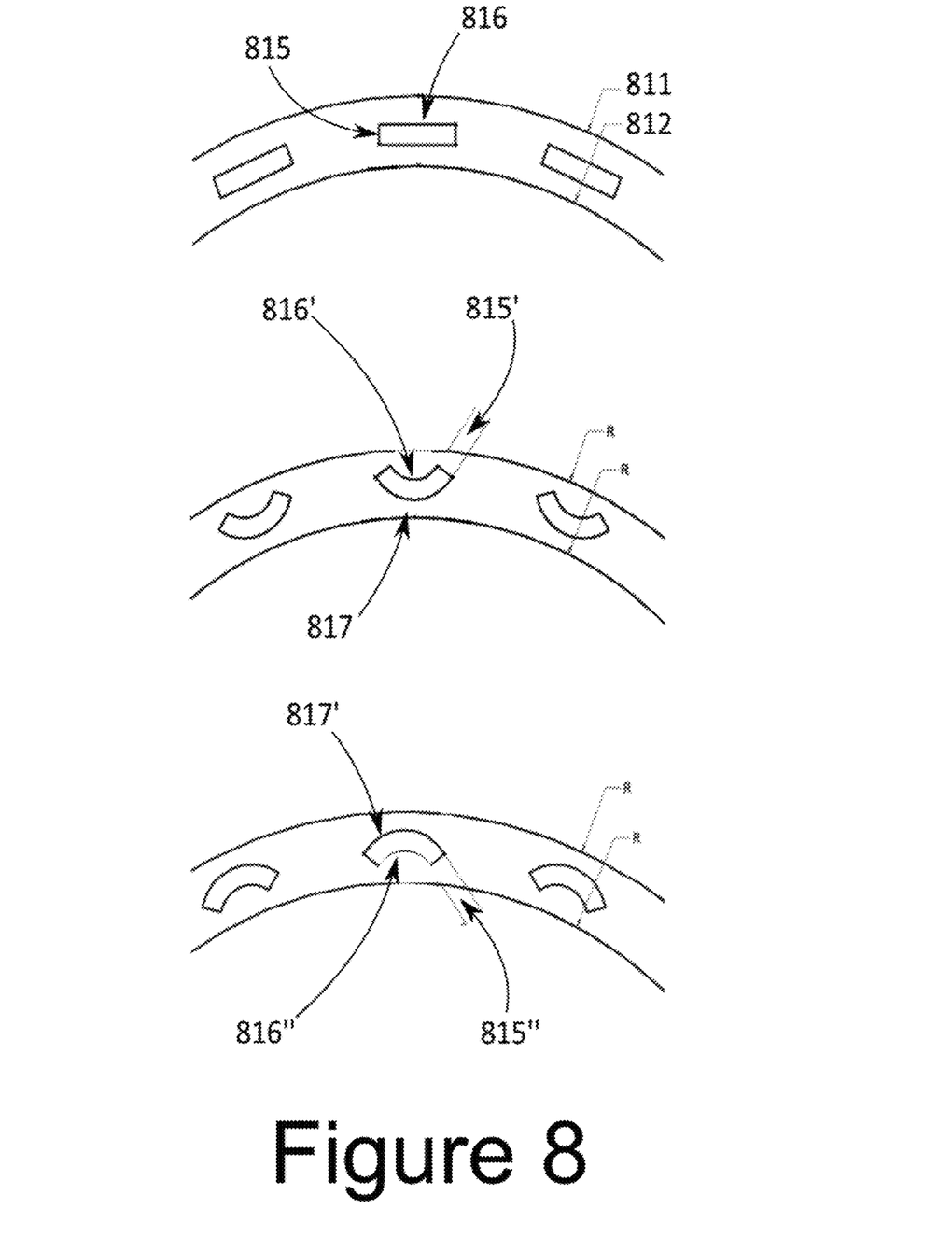
FIG. 8 is a cross-sectional view of a catheter and braid structure indicating the dimensions used in the Finite Element Analysis (FEA). The centroid of all geometries reside on the same radius of the composite.

For these calculations, the catheter wall is Pebax 7233. The OD radius 811 is 0.037" and the ID radius 812 is 0.032". Stainless steel is used for the wire or reinforcement member.

The calculations set out below use identical geometry. All wires have a thickness 815 of 0.0015" and mean width 816 of 0.0062". The ID/OD of the sheaths is the same, and the wires are situated at the same location in the sheath thickness—the centroid of wire geometry is on the same radius. This can be seen in FIG. 8.

For the calculation, the model catheter is centered above a curved part. The ends of the model are fixed except for axial movement. The calculation calculates the parameters of the catheter as the curved part moves upwards until the center section of the model catheter buckles, which shows up in the simulation by loss of convergence for the calculation.

The analysis calculates the amount of force necessary to achieve an increment of deflection at the center point of the model catheter.

This analysis does not take into account the improvements to the structural parameters created in the crescent-shaped wires when the wires are cold-rolled into their crescent shapes. Manufacturing the crescent shapes with the dimensions from this example yield a "¼ Hard" work range. When applied to 300 series stainless steel this yields a 75 ksi yield stress compared to the yield stress of the material before cold working of 31 ksi. This increase provides increased resistance to permanent deformation for the catheter. Thus, so forming the wires provides a passive benefit when used in the catheter in addition to the active one calculated in this example.

Comparative Example 1

FEA of Flat-Wire Catheter

The FEA model wires run axially down the composite, the most direct comparison given the large variety of braid patterns. It is inferred that axial-only comparisons between rectangular and crescent shapes yield the same relative performance as would braided versions with the same wire geometries. In both cases, the crescent wire will contribute a higher cross-sectional second area moment of inertia compared to rectangular wire.

Catheter with reinforcing wire having a rectangular cross-section. Wire thickness 815 is 0.0015". Mean wire width 816 is 0.00616". The wire framework has the wires arranged longitudinally and not braided.

Buckling begins at around 0.050" of deflection. The wire/sheath composite buckles at around 0.063" of deflection. The wires influence buckling to a much greater extent than the sheaths do. The maximum bending force before the beginning of buckling is 0.94 lbf.

Prophetic Example 2

FEA of Crescent-Shaped-Wire Catheter-Concave Portion of Wire Facing Outward-Curved Up Wire Catheter with reinforcing wire having a crescent-shaped cross-section. Wire thickness 815' would be 0.0015". The width 816' of the wire on the concave side would be 0.0047" and the width 817 of the wire on the convex side would be 0.0076", giving a mean wire width of 0.00615". The wire framework would have the wires arranged longitudinally and not braided.

Buckling would begin at around 0.060" of deflection (20% higher than Comparative Example 1). The wires would buckle at around 0.075" of deflection (19% higher than Comparative Example 1). The maximum bending force before the beginning of buckling would be 0.96 lbf (2% higher than Comparative Example 1).

Prophetic Example 2

FEA of Crescent-Shaped-Wire Catheter-Concave Portion of Wire Facing Outward-Curved-Up Wire Catheter with reinforcing wire having a crescent-shaped cross-section. Wire thickness 815' would be 0.0015". The width 816' of the wire on the concave side would be 0.0047" and the width 817 of the wire on the convex side would be 0.0076", giving a mean wire width of 0.00615". The wire framework has the wires arranged longitudinally and not braided.

Buckling would begin at around 0.060" of deflection (20% higher than Comparative Example 1). The wires would buckle at around 0.075" of deflection (19% higher than Comparative Example 1). The maximum bending force before the beginning of buckling would be 0.96 lbf (2% higher than Comparative Example 1).

Prophetic Example 3

FEA of Crescent-Shaped-Wire Catheter-Concave Portion of Wire Facing Inward-Curved-Down Wire Catheter with reinforcing wire having a crescent-shaped cross-section. Wire thickness 815" would be 0.0015". The width 816" of the wire on the concave side would be 0.0047" and the width 817' of the wire on the convex side would be 0.0076", giving a mean wire width of 0.00615". The wire framework would have the wires arranged longitudinally and not braided.

Figure 9:
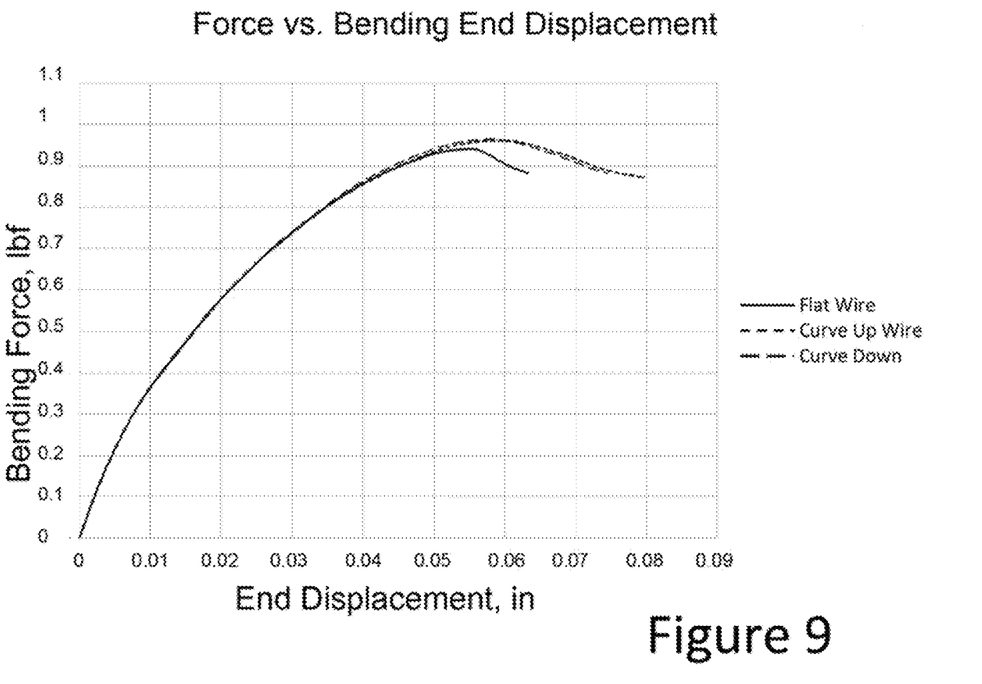
FIG. 9 is a chart of Force vs. Bending End Displacement for a flat wire braid structure, a curved-up braid structure, and a curved-down braid structure based on the FEA data. The geometry was displacement loaded in a 3 point bending situation, length of the sample 10 times the mean diameter. The ends of the lines of the graph represent the point of buckling which results in total occlusion of the sample lumen.

FIG. 9 graphs the data from the FEA analysis. As can be seen, the crescent wire braid structures demonstrate that the crescent wires withstand significantly more displacement before buckling and more bending force than the prior art flat wire braid structure.

Buckling would begin at around 0.060" of deflection (20% higher than Comparative Example 1). The wires would buckle at around 0.075" of deflection (19% higher than Comparative Example 1). The maximum bending force before the beginning of buckling would be 0.96 lbf (2% higher than Comparative Example 1).

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true, intended, explained, disclosed, and understood scope and spirit of this invention's multitudinous embodiments and alternative descriptions.

Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

What is claimed is:

1. A catheter comprising:
   a base material contacting a braid structure having a plurality of crescent ribbons disposed about a luminal axis of the catheter;
   wherein buckling of the braid structure begins at around 0.060 inches of deflection.

2. The catheter of claim 1 wherein the concave side of the crescent ribbons face luminally.

3. The catheter of claim 2 wherein at least one crescent ribbon comprises any one or any combination of metals including a cold-worked metal, a stressed metal, or an annealed metal.

4. The catheter of claim 3 wherein the crescent ribbons comprise any one or any combination of biocompatible metals.

5. The catheter of claim 4 wherein the base material is any one or any combination of conventional biocompatible polymers and copolymers.

6. The catheter of claim 5 wherein the base material is any one or any combination of polyurethanes, silicones, polyethers, thermoset polymeric material, polyesters, polyamides, fluoropolymers, polyolefins, PVC, polyimides, or PEEK.

7. The catheter of claim 6 wherein the base material is a film and the film contacts the braid structure on an inside of the braid structure, on an outside of the braid structure, or on the inside and the outside of the braid structure.

8. The catheter of claim 2 wherein the crescent ribbons consist essentially of metals.

9. The catheter of claim 8 wherein the base material is any one or any combination of conventional biocompatible polymers and copolymers.

10. The catheter of claim 9 wherein the base material is any one or any combination of polyurethanes, silicones, polyethers, thermoset polymeric material, polyesters, polyamides, fluoropolymers, polyolefins, PVC, polyimides, or PEEK.

11. The catheter of claim 10 wherein the base material is a film and the film contacts the braid structure on an inside of the braid structure, on an outside of the braid structure, or on the inside and the outside of the braid structure.

12. The catheter of claim 1 wherein the concave side of the crescent ribbons face abluminally.

13. The catheter of claim 12 wherein the crescent ribbons comprise any one or any combination of metal including a cold-worked metal, a stressed metal, or an annealed metal.

14. The catheter of claim 13 wherein the crescent ribbons comprise any one or any combination of biocompatible metals.

15. The catheter of claim 14 wherein the base material is any one or any combination of conventional biocompatible polymers and copolymers.

16. The catheter of claim 15 wherein the base material is any one or any combination of polyurethanes, silicones, polyethers, thermoset polymeric material, polyesters, polyamides, fluoropolymers, polyolefins, PVC, polyimides, or PEEK.

17. The catheter of claim 16 wherein the base material is a film and the film contacts the braid structure on an inside of the braid structure, on an outside of the braid structure, or on the inside and the outside of the braid structure.

18. The catheter of claim 17 wherein the crescent ribbons consist essentially of metals.

19. The catheter of claim 18 wherein the base material is any one or any combination of conventional biocompatible polymers and copolymers.

20. The catheter of claim 19 wherein the base material is any one or any combination of polyurethanes, silicones, polyethers, thermoset polymeric material, polyesters, polyamides, fluoropolymers, polyolefins, PVC, polyimides, or PEEK.

21. The catheter of claim 20 wherein the base material is a film and the film contacts the braid structure on the inside of the braid structure, on the outside of the braid structure, or on the inside and the outside of the braid structure.

22. The catheter of claim 1, wherein the wires of the braid structure buckle at around 0.075 inches of deflection.

23. The catheter of claim 1, wherein the maximum bending force before the braid structure begins buckling is 0.96 lbf.

24. The catheter of claim 1, wherein crescent ribbons include a cross-sectional thickness of 0.0015 inches.

25. The catheter of claim 24, wherein the crescent ribbons include a first width of 0.0047 inches on a concave side and a second width of 0.0076 inches on a convex side.

26. The catheter of claim 25, wherein the crescent ribbons include a mean wire width of 0.00615 inches.

* * * * *